US00PP23481P2

(12) United States Plant Patent
van Opstal

(10) Patent No.: US PP23,481 P2
(45) Date of Patent: Mar. 19, 2013

(54) ***PIERIS* PLANT NAMED 'OPSTAL 10'**

(50) Latin Name: *Pieris japonica*
Varietal Denomination: Opstal 10

(76) Inventor: Ronnie Adrianus Antonius van Opstal, Zundert (NL)

( * ) Notice: Subject to any disclaimer, the term of this patent is extended or adjusted under 35 U.S.C. 154(b) by 0 days.

(21) Appl. No.: 13/373,650

(22) Filed: Nov. 23, 2011

(51) Int. Cl.
*A01H 5/00* (2006.01)

(52) U.S. Cl. ..... Plt./226

(58) Field of Classification Search ..... Plt./226
See application file for complete search history.

*Primary Examiner* — Annette Para
(74) *Attorney, Agent, or Firm* — Penny J. Aguirre

(57) ABSTRACT

A new cultivar of *Pieris*, 'Opstal 10', that is characterized by its leaves that are variegated with deep green center and creamy yellow margins with the leaf tips young leaves red-purple and its large inflorescences with flowers that open light pinkish red in color and mature to white and lightly suffused with light pink near the apex.

2 Drawing Sheets

Genus/species: *Pieris japonica*.
Varietal denomination: 'Opstal 10'.

BACKGROUND OF THE INVENTION

The present invention relates to a new and distinct cultivar of *Pieris japonica* and will be referred to hereafter by its cultivar name, 'Opstal 10'. 'Opstal 10' represents a new cultivar of *Pieris*, an evergreen shrub grown for landscape use.

The new *Pieris* arose as a naturally occurring branch mutation of 'Rato' (U.S. Plant Pat. No. 19,331) in Zundert, The Netherlands in January 2006.

Asexual reproduction of the new cultivar was first accomplished by softwood cuttings in 2206 in Zundert, The Netherlands by the Inventor. The characteristics of this cultivar have been determined to be stable and are reproduced true to type in successive generations.

SUMMARY OF THE INVENTION

The following traits have been repeatedly observed and represent the characteristics of the new *Pieris*. These attributes in combination distinguish 'Opstal 10' as a unique and distinct cultivar of *Pieris*.

1. 'Opstal 10' exhibits leaves that are variegated with deep green center and creamy yellow margins with the leaf tips young leaves red-purple.
2. 'Opstal 10' exhibits large inflorescences with flowers that open light pinkish red in color and mature to white and lightly suffused with light pink near the apex.

'Opstal 10' can most closely compared to its parent plant, 'Ralto'. 'Ralto' differs from 'Opstal 10' in having flowers that are darker reddish pink and mature to a light pink color. 'Opstal 10' can also be compared to the cultivars 'Flaming Silver' (not patented) and 'Variegata' (not patented). 'Flaming Silver' differs from 'Opstal 10' in having young and mature flowers that are white in color and in having young leaf tips that are light orange in color. 'Variegata' differs from 'Opstal 10' in having young and mature white flowers.

BRIEF DESCRIPTION OF THE DRAWING

The accompanying photographs were taken of a three year-old plant of 'Opstal 10' as grown outdoors in a 2-liter container in Zundert, The Netherlands and are representative of the new *Pieris*.

The photograph in FIG. 1 provides a side view of a plant of 'Opstal 10' in bloom.

Figure 1:
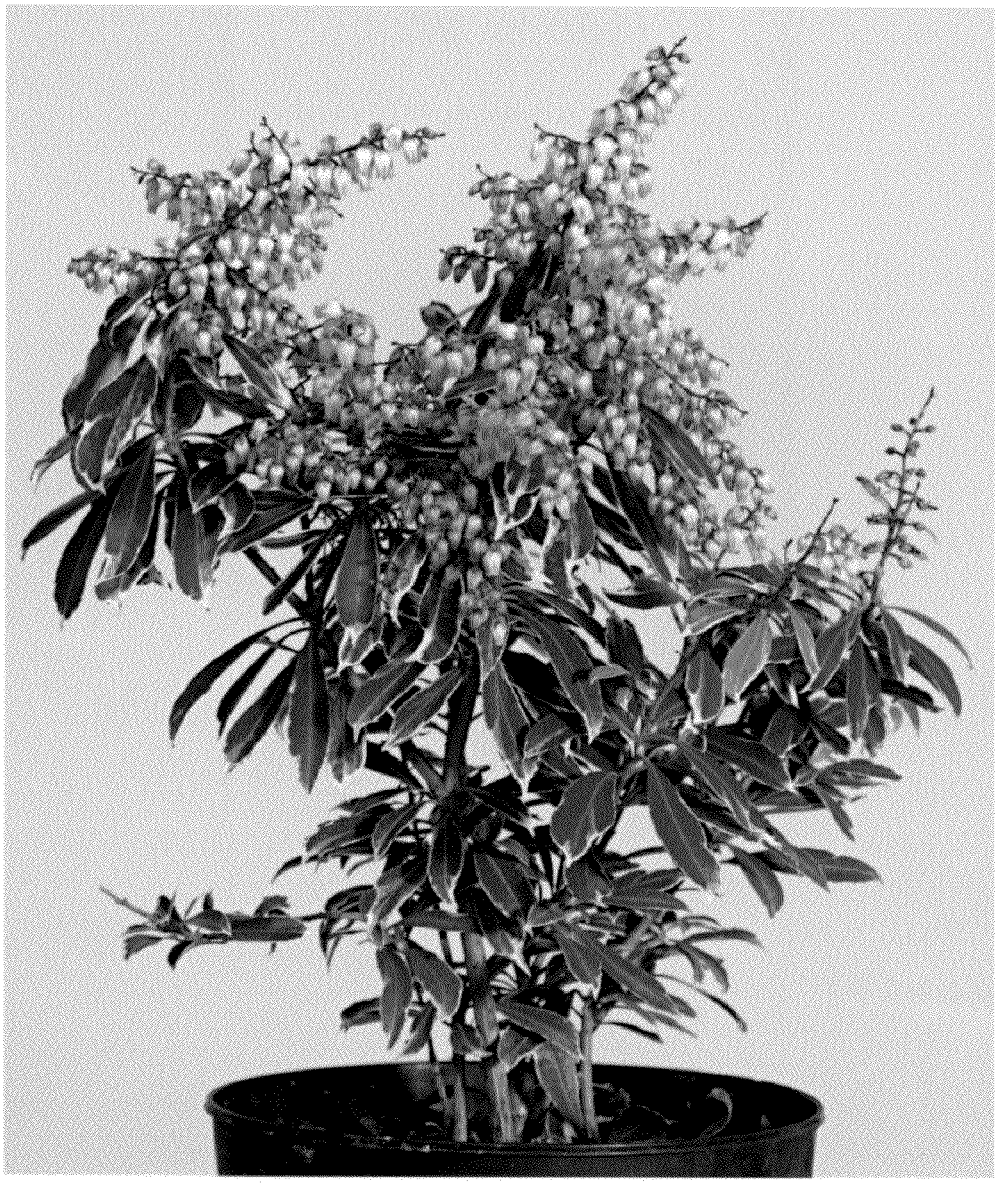
Figure 2:
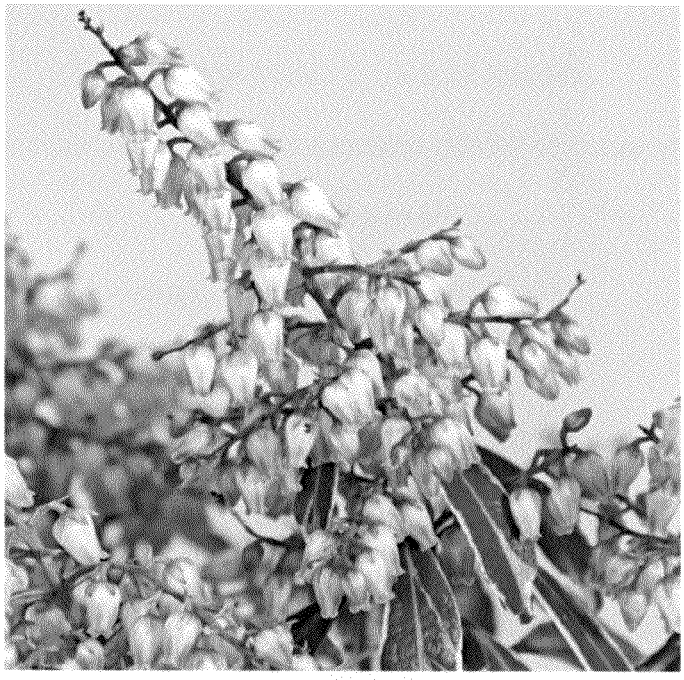

The photograph in FIG. 2 provides a close-up view of an inflorescence of 'Opstal 10'.

Figure 3:
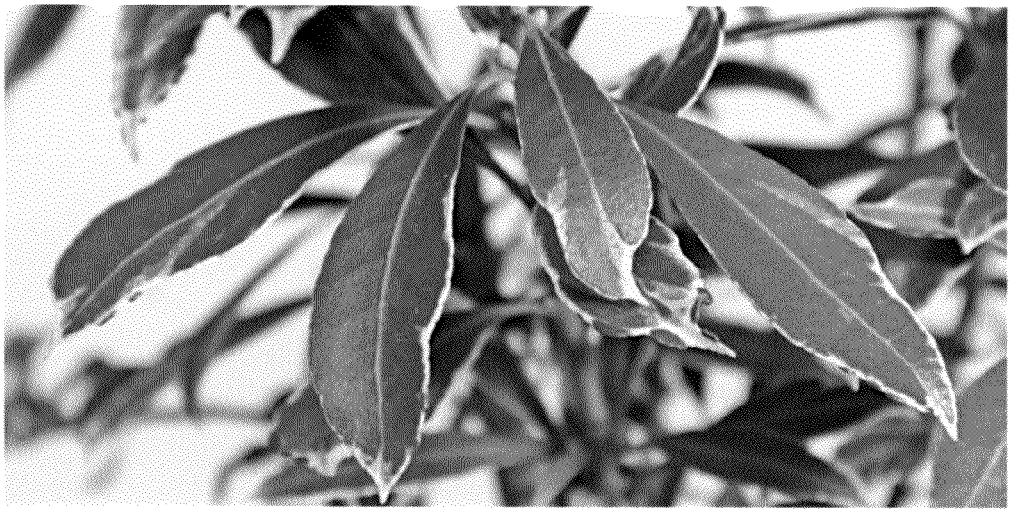

The photograph in FIG. 3 provides a close-up view of the foliage of 'Opstal 10'.

The colors in the photographs are as close as possible with the digital photography and printing techniques utilized and the color codes in the detailed botanical description accurately describe the colors of the new *Pieris*.

BOTANICAL DESCRIPTION OF THE PLANT

The following is a detailed description of three year-old plants of the new cultivar as grown outdoors in 2-liter containers in Zundert, The Netherlands. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Plant type.*—Evergreen shrub.
*Plant habit.*—Upright and spreading.
*Blooming period.*—4 weeks in early spring.
*Height and spread.*—An average of 30.7 cm in height and 25.9 cm in spread.
*Hardiness.*—At least hardy to U.S.D.A. Zones 6.
*Diseases and pest resistance.*—Not more susceptible to pests and diseases than other *Pieris* varieties.
*Propagation.*—Softwood stem cuttings.
*Roots.*—Thin and fibrous, moderately branched.
*Growth rate.*—Vigorous.

Branch description:

*Branch color.*—New growth 143B, mature wood a blend of 199A and 199B.
*Branch shape.*—Rounded, slightly angulate.
*Branch size.*—Lateral branches; an average of 9.8 cm in length and 2.5 mm in diameter, internode; average of 4 mm in length.
*Branch surface.*—Smooth and moderately glossy.

*Branching.*—Average of 13 lateral branches, strong stem strength.

Foliage description:

*Leaf shape.*—Oblanceolate.

*Leaf division.*—Simple.

*Leaf base.*—Attenuate.

*Leaf apex.*—Apiculate to cuspidate.

*Leaf venation.*—Anastomosing,146B on upper surface, 144A on lower surface.

*Leaf margin.*—Shallowly and irregular crenate.

*Leaf attachment.*—Petiolate.

*Leaf arrangement*—Alternate, leaves mainly clustered at branch tips.

*Leaf texture.*—Smooth and glossy on upper and lower surface.

*Leaf size.*—An average of 4.4 cm and 1.6 cm in width.

*Leaf number.*—About 25 per lateral branch.

*Internode length.*—An average of 4 mm.

*Leaf color.*—Young upper surface; 175A, margins near the tip; 58D, main vein; 144B, young lower surface; 174A to 174B margins near the tip; ranging from 58D to 182D, main vein; 144B, mature upper surface; N137A with blotches; a blend of 191B to 191C and 194B, margins a blend of 4C and 8C, mature lower surface; 138A and 138B with blotches; 191A and 191B, margins; 5D.

*Petioles.*—About 9 mm in length and 1 mm in width, 144B in color, surface glabrous.

*Stipules.*—None.

Flower description:

*Inflorescence type.*—Terminal paniculate racemes.

*Inflorescence size.*—Up to 8.7 cm in height and 7.5 cm in width.

*Inflorescence lastingness.*—About 2 weeks.

*Flower type.*—Closed campanulate, urn-shaped.

*Flower fragrance.*—Sweet and pleasant.

*Flower bud description.*—Ovate in shape, about 6 mm in length and 3 mm in diameter, bud; N155B and N155C in color and heavily suffused with 63B and 63C, immature calyx; between 185C and 185D in color.

*Flower quantity.*—An average of 180 per inflorescence.

*Flower size.*—About 7 mm in depth and diameter.

*Peduncle.*—About 8.3 cm in length and 1.2 mm in diameter, 146A to 146B in color, primary peduncle angle; 0°, secondary peduncle angle; 90° to primary peduncle, glabrous surface.

*Pedicels.*—About 6 mm in length and 0.5 mm in diameter, 177C in color, glabrous surface.

*Petal description.*—5, ovate in shape, margin is entire, apex is obtuse, lower and upper surface is smooth, dull and slightly ribbed lengthways, about 7.5 mm in length and 2 mm in width base fused (upper 7% are free), color; upper surface when opening; N155B and heavily suffused with 63B and 63C, lower surface when opening; N155B and heavily suffused with 68B, upper surface fully opened; N155B with apex lightly suffused with 63C to 63D, lower surface fully opened; N155B with apex lightly suffused with 68C.

*Calyx.*—Rotate, average of 2 mm in length and 5 mm in diameter.

*Sepal description.*—5, ovate in shape, margin is entire, apex is acute, base is broad cuneate, surface is glabrous on upper and lower surface, an average of 3 mm in length and 1 mm in width, color; immature upper side; 185C and 185D, mature lower side; 182B and 182D.

Reproductive organs:

*Gynoecium.*—1 Pistil, about 45 mm in length, stigma is narrow club-shaped and N144B in color, style is about 4 mm in length and 145D in color, ovary is 144C in color.

*Androecium.*—10, anthers are dorsifixed in shape, about 1 mm in length and 200A to 200C in color with 2 hairs extending from anthers about 1 mm in length and 175A and 175B in color, pollen is very low and N167C in color.

*Fruit and seed.*—Fruit or seed was not observed.

It is claimed:

1. A new and distinct cultivar of *Pieris* plant named 'Opstal 10' substantially as herein illustrated and described.

* * * * *